United States Patent [19]

Martinez Ubeira

[11] Patent Number: 5,578,490
[45] Date of Patent: Nov. 26, 1996

[54] CELL CULTURE PLATE WITH A SYSTEM FOR LATERAL DIFFUSION OF MOLECULES THROUGH A BARRIER MEMBRANE

[75] Inventor: Florencio Martinez Ubeira, Santiago de Compostela, Spain

[73] Assignee: Universidade de Santiago de Compostela, Spain

[21] Appl. No.: 244,092

[22] PCT Filed: Sep. 14, 1993

[86] PCT No.: PCT/ES93/00074

§ 371 Date: Jul. 18, 1994

§ 102(e) Date: Jul. 18, 1994

[87] PCT Pub. No.: WO94/06902

PCT Pub. Date: Dec. 31, 1994

[30] Foreign Application Priority Data

Sep. 16, 1992 [ES] Spain ................................ P9201859

[51] Int. Cl.⁶ ................................................ C12M 3/02
[52] U.S. Cl. ................... 435/287.1; 435/305.2; 435/305.3; 422/101; 422/102
[58] Field of Search ..................... 435/286, 297, 435/298; 422/101, 102

[56] References Cited

U.S. PATENT DOCUMENTS 3,221,878 12/1965 Brett ........................................... 210/94
3,985,608 10/1976 Saxholm ................................... 195/127
4,636,473 1/1987 Kleinstreuer ............................ 435/289
4,975,377 12/1990 Key ........................................... 435/284

FOREIGN PATENT DOCUMENTS 0252333 1/1988 European Pat. Off. ......... C12M 3/00
8809806 12/1988 WIPO .............................. C12M 1/20

Primary Examiner—David A. Redding
Attorney, Agent, or Firm—Ostrolenk, Faber, Gerb & Soffen, LLP

[57] ABSTRACT

A cell culture plate with a system for lateral diffusion of molecules across a barrier membrane (FIG. 1), comprising a base consisting of two or more flat-bottomed open-topped wells, denominated the reservoir wells, each containing one or more wells of smaller size (diffusion wells), likewise open-topped and sharing the same flat base, characterized in that each of the diffusion wells communicates with the larger reservoir well which houses it via one or several slits located in the lateral wall(s) of the diffusion well(s), and in that each slit is covered by a semipermeable membrane that permits the passage of soluble substances while retaining insoluble particles and cells; and a removable lid. The cells deposited in the diffusion well(s) may interchange their metabolic products with the corresponding reservoir well containing culture medium or other cells. The problem caused by other devices wherein the diffusion of substances occurs between a higher compartment (which usually contains the cells) and a lower compartment, separated by a barrier membrane, making difficult the microscopic observation of the cells and the manipulation thereof, is thus solved. The fields of application include various branches of biology, such as immunology, pharmacology, toxicology, microbiology and parasitology.

5 Claims, 7 Drawing Sheets

CELL CULTURE PLATE WITH A SYSTEM FOR LATERAL DIFFUSION OF MOLECULES THROUGH A BARRIER MEMBRANE

DESCRIPTION

A cell culture plate with a system for lateral diffusion of molecules across a barrier membrane.

In the course of biological experimentation, it is frequently necessary to culture one or several cell populations at high cell density and under low oxygen concentration. In such circumstances it is necessary to use special techniques, with the aim of supplying metabolically active cells with the necessary nutrients and of maintaining pH within physiological limits.

To date, these objectives have been achieved either by daily supplementation of cultures with fresh nutrients and with an alkaline substance which corrects the excess acidity of the culture (procedure A), or by the use of special culture plates in which the cells are cultured on a permeable membrane, the cell metabolites passing across this membrane into a reservoir of culture medium (procedure B).

The two procedures described have two major disadvantages:

Under procedure A, the metabolites produced by the cells are not removed, and thus may accumulate to levels which are toxic for the cultured cells. The procedure is very time consuming, and the need for daily handling of cultures increases the risk of contamination. The daily addition of an alkaline substance in order to correct pH leads to abrupt fluctuations in this parameter, and this may prove harmful to the cultured cells.

Under procedure B, the need to culture cells on a permeable membrane makes it difficult or impossible a) to harvest the cells (particularly cells that adhere to the membrane), b) to examine the cells under a microscope (since observation must be across both the culture medium reservoir and the membrane), and c) to carry out multistage cultures (eg. in situations in which it is necessary to maintain the cells in contact with a given substance for a given period of time).

In the culture plate 10 fitted with a lateral diffusion system (FIG. 1), two flat-bottomed open-topped wells, denominated the reservoir well 12 and the diffusion well 14, communicate via two slits 16, 18 situated in the lateral wall/s 20 of the diffusion well 14. Each of these slits 16,18 is covered by a semipermeable membrane 22 which permits the transfer of soluble substances, but not of insoluble substances or cells, between the two wells. Transfer of cell metabolic products from the diffusion well to the reservoir well, and of culture medium from the reservoir well to the diffusion well, may thus occur. In existing apparatuses based on basal diffusion, in which substances diffuse across a semipermeable membrane between an upper compartment (typically that containing the cells) and a lower compartment, both microscopic observation and cell handling are very difficult: these problems are overcome by the present invention. The present invention has two additional advantages over existing apparatuses based on basal diffusion. Firstly, the surface tension at the outside of the membrane 22 located in the lateral walls 20 of the diffusion well 14 of the present invention compensates for the hydrostatic pressure on the inside, preventing leakage of liquid from the diffusion well 14 when the reservoir well 12 is empty. This allows cells to be incubated with soluble substances for a given period, during which diffusion to the reservoir is not permitted. Secondly, in the present invention, in which the cultured cells are layered upon the plastic base of the diffusion well, the diffusion of cell metabolites and other soluble substances from the diffusion well to the reservoir well occurs more slowly than in existing apparatuses based upon basal diffusion, in which the semipermeable membrane is larger in area and in which the basal surface of the cell layer rests directly upon the membrane. In the present invention, therefore, the diffusion of substances from the diffusion well 14 to the reservoir well 12 occurs sufficiently rapidly to ensure the maintenance of physiological conditions but sufficiently slowly to delay the removal of substances necessary for cell growth or differentiation, such as growth factors. Cell culture by means of the present invention thus combines the advantages of procedures A and B, and at the same time lacks the majority of the disadvantages of these two procedures.

The preferred embodiment (FIG. 2) consists of: a) a parallelepipedal base [5] comprising multiple flat-bottomed open-topped wells, denominated reservoir wells [6] (in the figure only a single well is shown), each of which contains another well (preferably cylindrical), likewise open-topped and flat-bottomed, denominated a diffusion well [3], in whose walls two openings or windows [4] have been made, these being diametrically opposed and sealed with a semipermeable membrane; b) a removable lid [1] which does not create an airtight seal and thus allows movement of gases into and out of the apparatus on the path indicated by interrupted schematic path. Optionally, the inner surface of the lid may bear raised rings [2] which, on placing the lid over the apparatus, act as individual lids for the reservoir wells and/or the diffusion wells (in FIGS. 2, 6, 7 and 8, the apparatus has such individual lids for the diffusion wells), thus preventing condensation from dripping off the inner surface of the lid [1] into the cultures. With reference to FIG. 3, the diffusion wells may be at different heights or levels compared to those of the reservoir wells.

EXAMPLE

FIG. 3 shows one possible embodiment of the present invention, consisting of a plate with six rectangular compartments (reservoir wells), each of which contains a cylindrical compartment (diffusion well) containing two slits or windows to which two semipermeable membranes are subsequently fixed. These membranes permit the passage of soluble substances but not cells or particulate matter. With the exception of the membranes, which are attached subsequently, the entire plate is constructed, with the aid of an appropriate mould, from a single sheet of transparent polystyrene of suitable characteristics for cell culture. The apparatus also has a rectangular lid, similarly constructed from a single sheet of transparent polystyrene (FIG. 6). As shown in FIGS. 6 and 7, the lid bears six raised rings (of diameter somewhat greater than that of the diffusion wells) on its inner surface, so that on positioning the lid over the base each ring acts as an individual lid for a diffusion well to prevent dripping of condensation from the inner surface of the rectangular lid into the culture. In addition, in order to facilitate the diffusion of gases between the cultures and the incubator chamber, the rectangular lid has a small triangular elevation at each of its corners (letter V in FIGS. 7 and 8); these elevations rest upon the corresponding upper corners of the wall of the base plate, ensuring that a small space remains between the base plate and the lid, and thus ensuring free movement of gases (as shown in FIG. 2).

Figure 1:
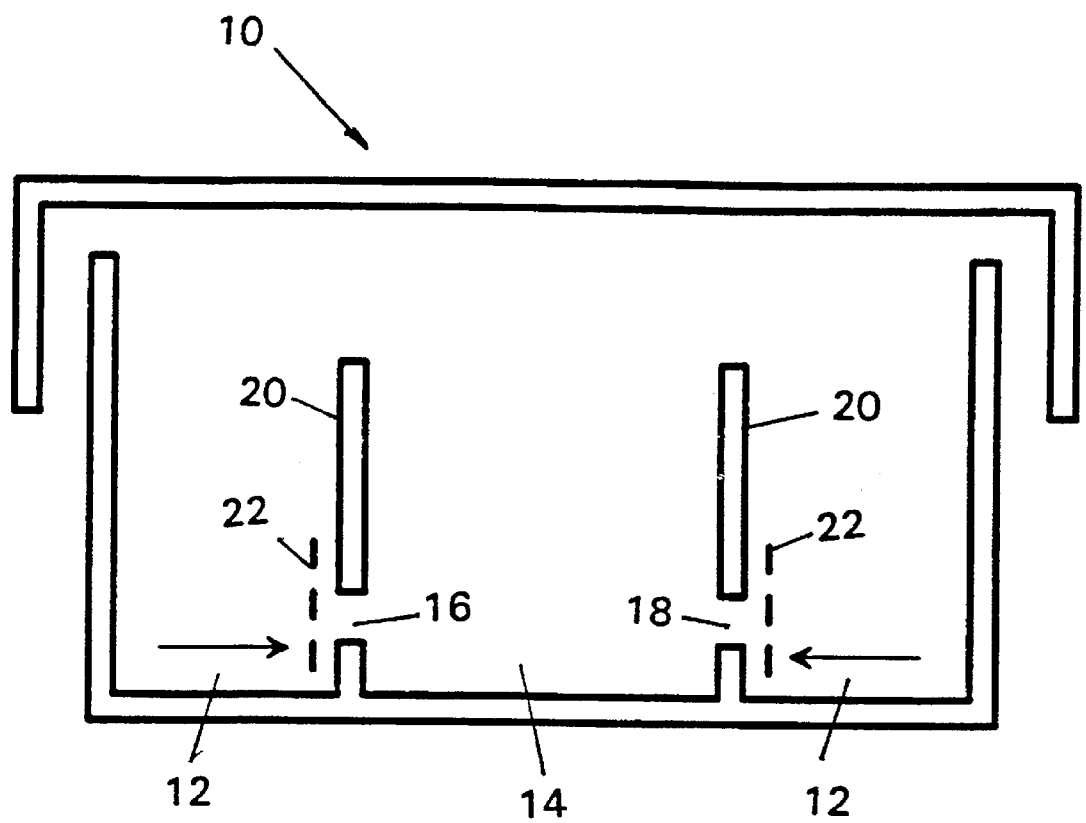
FIG. 1 is a schematic cross-sectional view of the lateral diffusion system for a culture plate comprising a single reservoir well and a single diffusion well.
Figure 2:
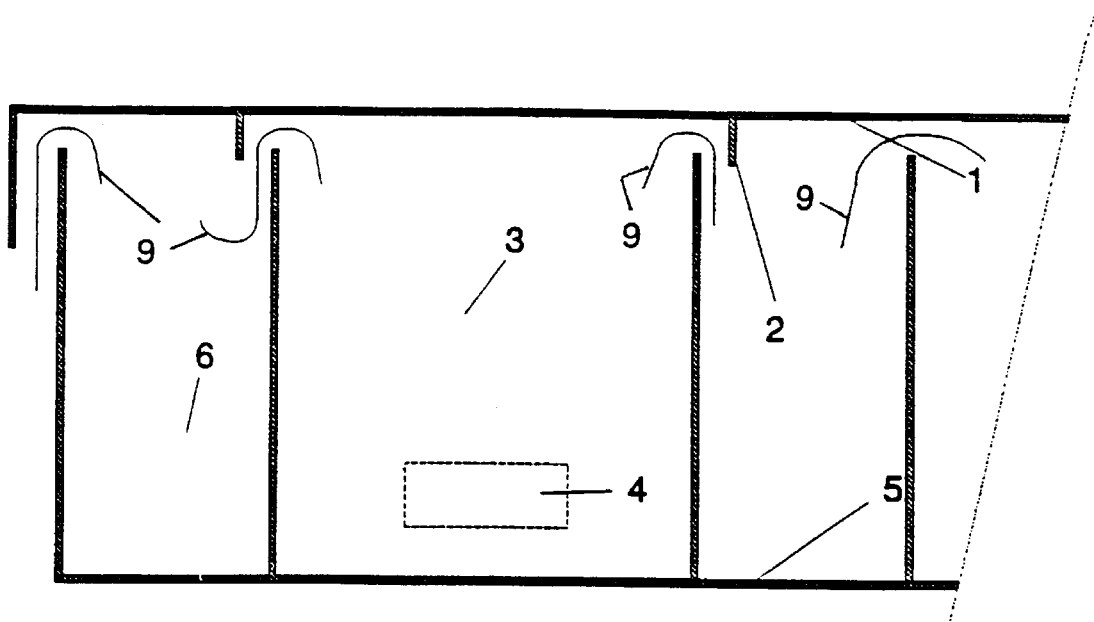
FIG. 2 is a schematic cross-sectional view showing the various components of the culture plate and indicating how movement of gases may occur (multiwell plate).
Figure 3:
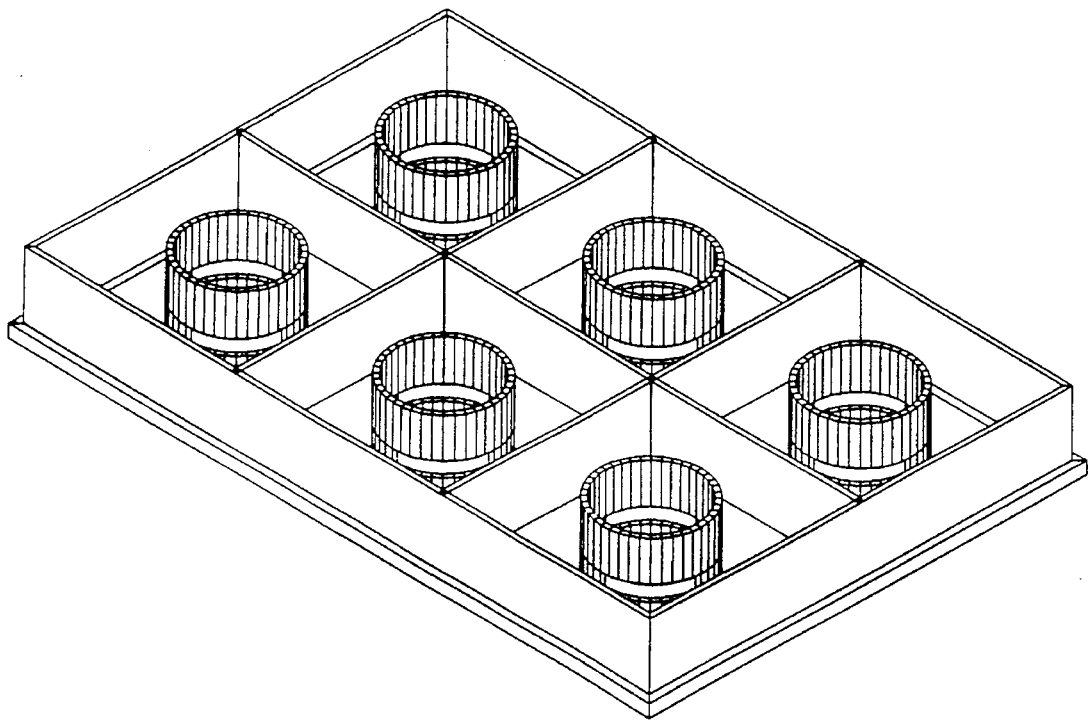
FIG. 3 is a perspective view of the base plate showing the arrangement of the compartment (multiwell plate).
Figure 4:
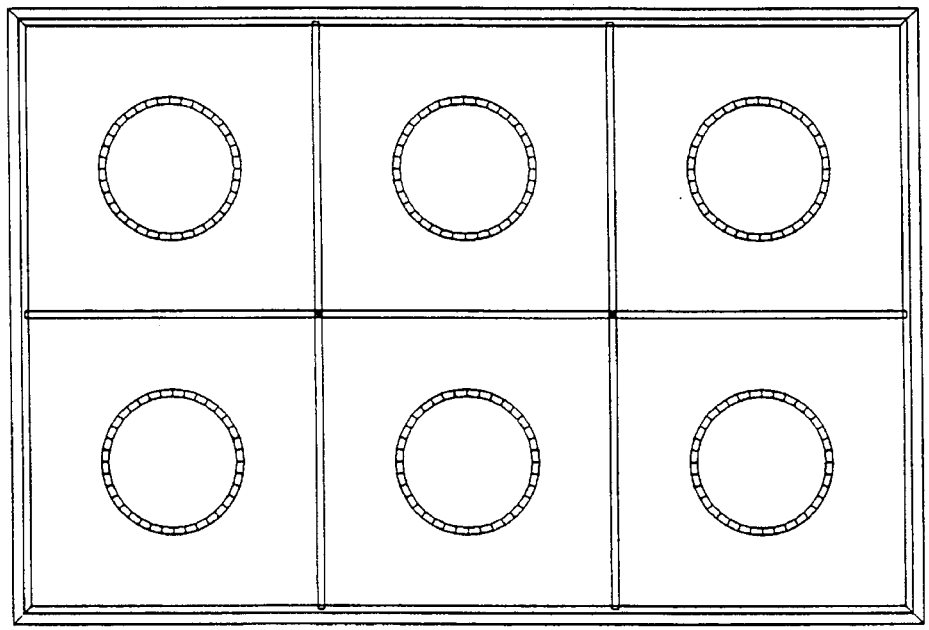
FIG. 4 is a view from above showing the basic lay-out of a multiwell plate.
Figure 5:
FIG. 5 is a side view of a multiwell plate.
Figure 6:
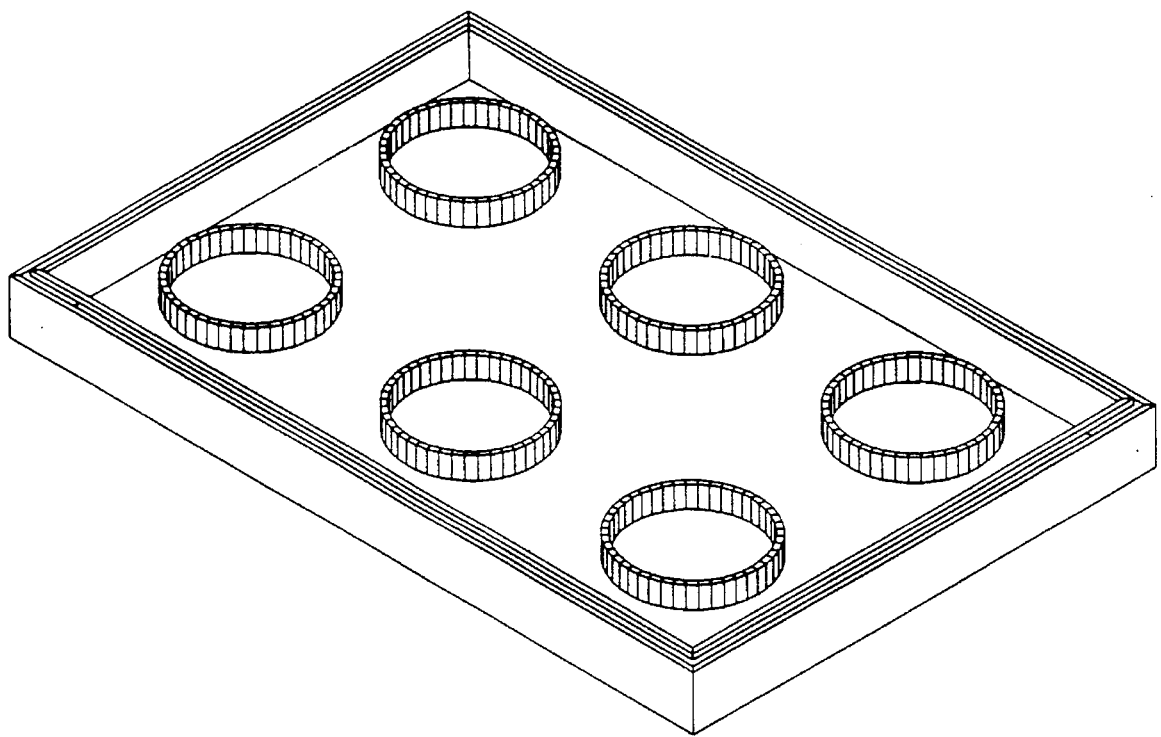
FIG. 6 is a perspective view of the lid of a multiwell plate.
Figure 7:
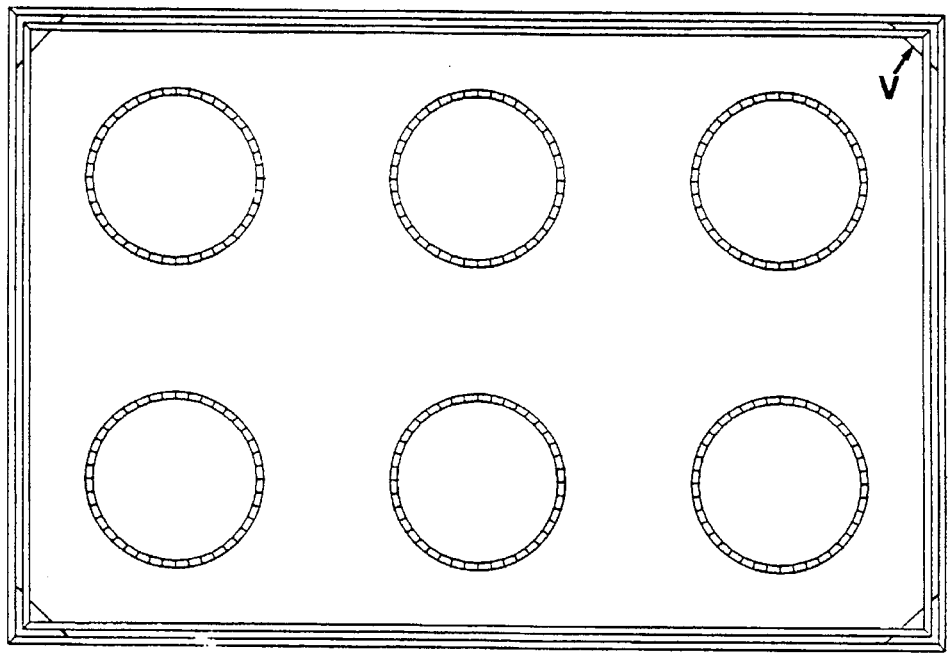
FIG. 7 is a view from above showing the basic lay-out of the lid of a multiwell plate.
Figure 8:
FIG. 8 is a side view of the lid of a multiwell plate.
Figure 9:
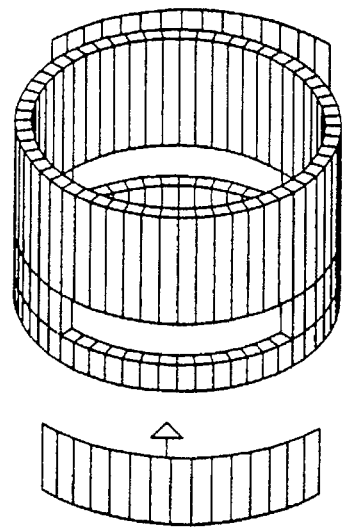
FIG. 9 is an exploded perspective view of a single diffusion well showing the slits or windows over which the semipermeable membranes are fitted.
Figure 10:
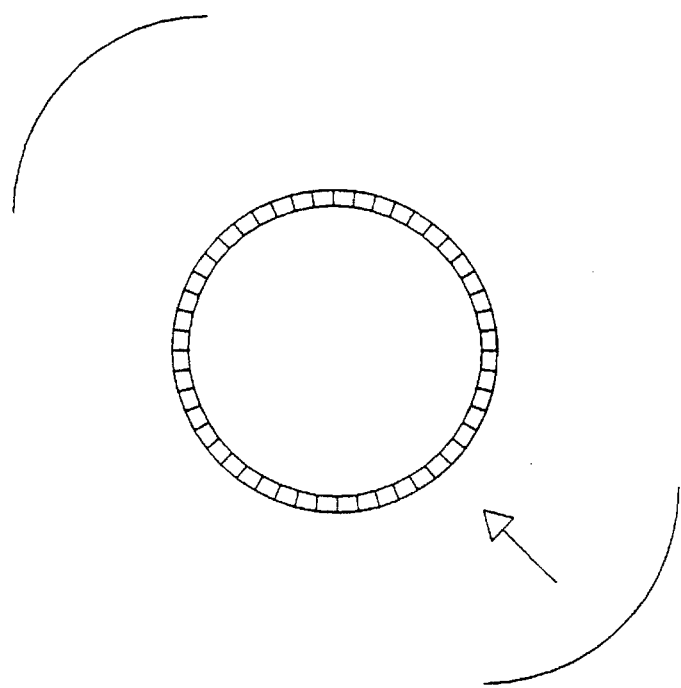
FIG. 10 is an exploded view from above of a single diffusion well.
Figure 11:
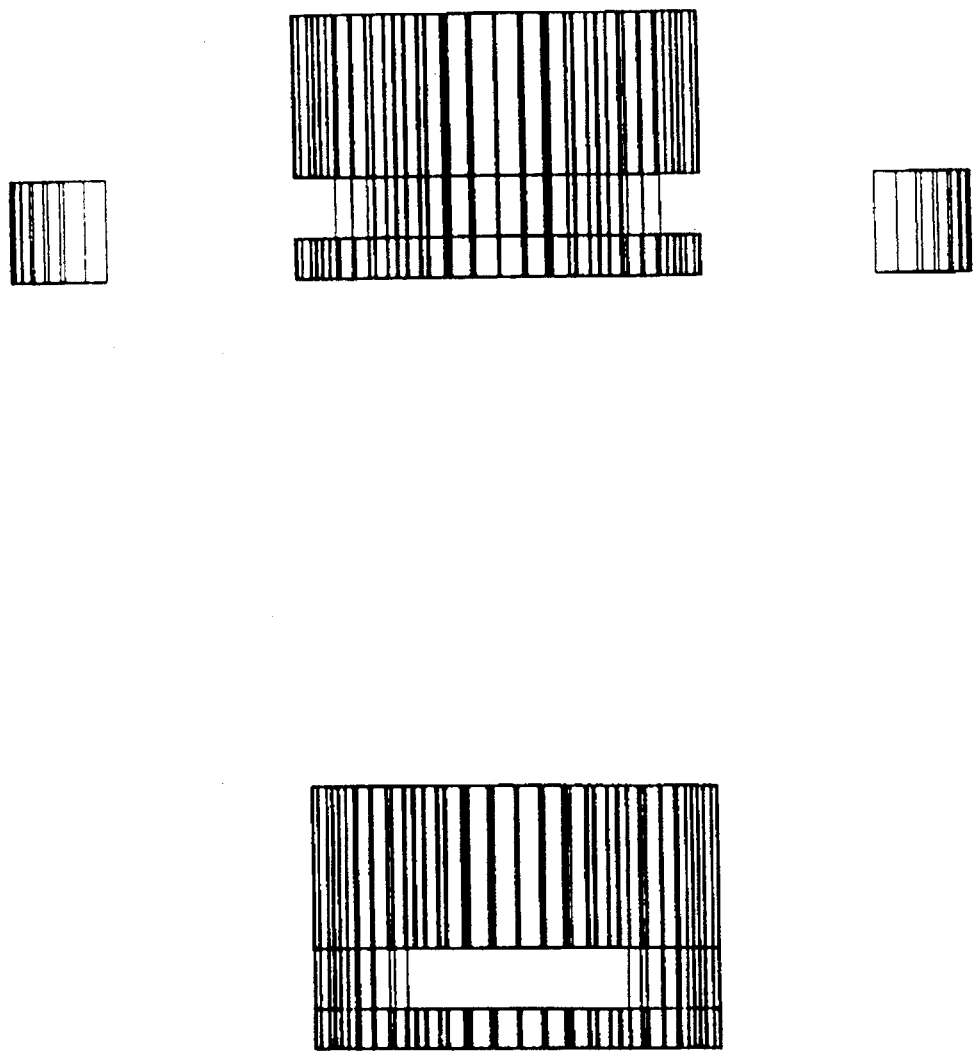
FIG. 11 is a) an exploded side view of a single diffusion well oriented with the slits to either side of center, and b) a side view of a single diffusion well oriented with the slits at centre.

The potential applications at the present invention include the following.

1) Immunology
a) In vitro induction of primary and secondary immune responses;
b) Studies of cellular interactions mediated by soluble substances;
c) Studies of antigen presentation;
d) Studies of cell maturation;
e) Studies of immunomodulatory substances, etc.

2) Endocrinology
Studies of secretion of, and cellular responses to, hormones.

3) Pharmacology
Dotormination of the pharmacological activities and toxicity of drugs in cell cultures or in whole (unicellular or multicellular) organisms, etc.

4) Toxicology
Determination of the in vitro toxicity of compounds, etc.

5) Microbiology and parasitology
Studies of in vitro interactions between substances produced by parasites and cells.

I claim:

1. Cell culture plate fitted with a system for the lateral diffusion of molecules across a barrier membrane, comprising: a base consisting of an open-topped, flat-bottomed, reservoir well, said reservoir well containing another, smaller diffusion well, likewise open-topped and sharing the same flat base, characterized in that the two wells communicate via one or several slits or orifices located in at least one lateral wall of the diffusion well, and in that said slits or orifices are covered by semipermeable membranes; and a removable lid which when placed over the base allows the whole system to be closed though without creating an airtight seal.

2. Cell culture plate fitted with a system for the lateral diffusion of molecules through a barrier membrane, comprising: a base consisting of a number of open-topped, flat-bottomed reservoir wells, each reservoir well containing another diffusion well of smaller size, likewise open-topped and sharing the same flat base, characterized in that each of the diffusion wells communicates with the reservoir well which houses it via one or several slits or orifices located in a lateral wall of the diffusion well, and in that said slits or orifices are covered by semipermeable membranes; and a removable lid which when placed over the base allows the whole system to be closed though without creating an airtight seal.

3. Cell culture plate fitted with a system for the lateral diffusion of molecules across a barrier membrane, in accordance with claim 1, characterized in that the semipermeable membranes permit the passage of soluble substances while retaining insoluble particles and cells.

4. Cell culture plate fitted with a system for the lateral diffusion of molecules across a barrier membrane, in accordance with claim 1, characterized in that the barrier of the diffusion wells may be at different heights or levels to those of the reservoir wells.

5. Cell culture plate fitted with a system for the lateral diffusion of molecules across a barrier membrane, in accordance with claim 1, characterized in that a single reservoir well may be simultaneously in communication with various diffusion wells located in its interior.

* * * * *